United States Patent [19]
Davis et al.

[11] Patent Number: 4,799,927
[45] Date of Patent: Jan. 24, 1989

[54] NEEDLE GUIDE AND PUNCTURE PROTECTOR

[76] Inventors: Donald F. Davis, 7411 SW. 147 Ct., Miami, Fla. 33193; Stuart Brodsky, 1600 Catron SE., Albuquerque, N. Mex. 85710; Jeffrey Houska, 7204 Bangor NW., Albuquerque, N. Mex. 87120

[21] Appl. No.: 123,829

[22] Filed: Nov. 23, 1987

[51] Int. Cl.⁴ .............................................. A61M 5/32
[52] U.S. Cl. ..................................... 604/192; 604/263
[58] Field of Search ........................ 604/192, 263, 187

[56] References Cited

U.S. PATENT DOCUMENTS 4,485,918  12/1984  Mayer ............................. 604/263 X
4,623,336  11/1986  Pedicano et al. ................... 604/192
4,645,034  3/1987   Masters et al. ..................... 604/192

*Primary Examiner*—John D. Yasko
*Attorney, Agent, or Firm*—John C. Malloy

[57] ABSTRACT

A needle cover of rigid plastic material to protectively jacket a medical injection needle after use which includes a tubular body having a closed end and an enlarged open end defining a mouth and a throat which converges to the needle socket portion with guide surfaces on the throat to guide a needle toward the socket.

4 Claims, 1 Drawing Sheet

NEEDLE GUIDE AND PUNCTURE PROTECTOR

FIELD OF THE INVENTION

This invention relates to injection needles and, more particularly to a needle cover with an enlarged mouth through which the needle is passed along a throat surface into jacketing relation for disposal of a needle.

BACKGROUND OF THE INVENTION

Recently there has been a growing concern about punctures from needles. Ordinarily, injection needles after once being used in hospitals, are disposed of. Oftentimes they are disposed of in a plastic needle cover which is connected to the needle barrel for this purpose. Because of the concern of punctures and "sticks" by used needles, there is a growing tendency of medical personnel to not properly dispose of used injection needles, that is not to position them properly in a protective tubular needle cover. One of the reasons for this is that there is a concern that the person positioning a needle cover over a used needle may inadvertently stick himself. This invention is of an improved needle cover with an enlarged mouth and which provides a rigid plastic protective throat extending and converging toward a needle socket. About the mouth, a protective lip may also be provided so that, if a needle is not inserted coaxially into the needle cover, there will be less likelihood of an injury by a needle puncture, because the needle cover will "catch" the needle more readily.

OBJECTS OF THIS INVENTION

It is an object of this invention to provide an improved needle cover which includes a needle receiving socket and an enlarged open mouth with a throat including guide means intended to guide a needle into coaxial nested relation within the needle cover after use of it.

In accordance with the general object, the instant invention will now be described with reference to the accompanying drawings in which:

DETAILED DESCRIPTION OF THE PREFERRED EMBODIMENT

Figure 1:
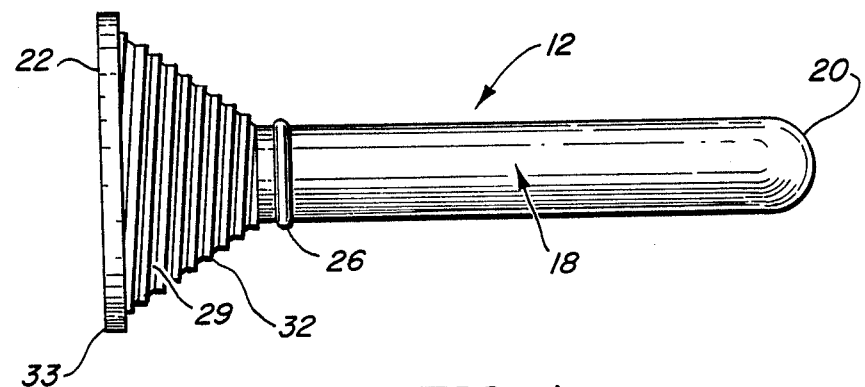
FIG. 1 is a side view of a needle cover in accordance with this invention.
Figure 2:
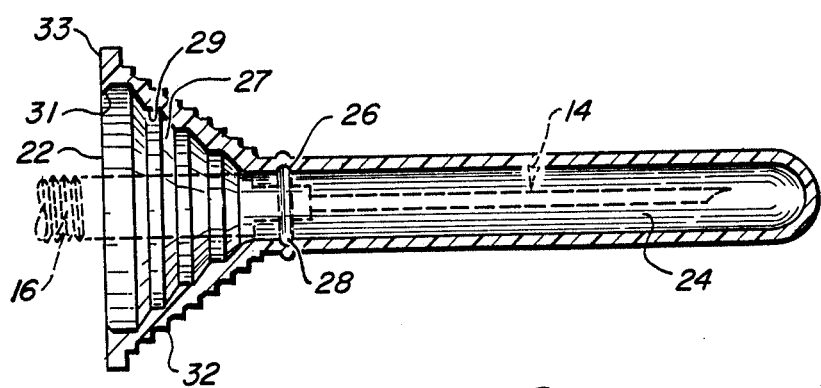
FIG. 2 is a view in cross-section of the needle cover shown in FIG. 1 and wherein knurling is provided on the exterior surface of the throat portion of the needle cover.

Referring to the drawings wherein like reference characters designate like or corresponding parts throughout the several views and referring particularly to FIG. 1, there is shown a needle cover generally designated by the numeral 12 It is of rigid plastic material and is adapted to receive and jacket a medical injection needle generally designated by the numeral 14 in FIG. 2 extending from one end of a needle barrel 16. The cover it is seen is composed of a generally tubular body 18 having a closed end 20 and an enlarged open end 22. There is defined a needle socket 24 extending from the closed end a distance greater than the needle to be received therein. There are means 26 on the tubular body to cooperate with means on the barrel to nestingly engage the barrel and to cooperate to maintain the needle in the socket protectively jacketed by the rigid plastic material of the needle cover. Referring now to the enlarged end 22 there is defined a mouth of at least about 3 centimeters in diameter. Extending from the open mouth there is a throat zone 27 which converges to the socket wall of the needle cover. This throat zone is preferably at least about 1/16 of an inch in thickness. The throat surface is provided with guide means on the surface to guide the needle toward the socket. In a preferred embodiment, the throat may be composed of successive rings, each smaller than the other in diameter proceeding from the open mouth to the socket diameter. In this embodiment, one of the rings has generally an axially extending inward face or surface while the next ring, of somewhat smaller diameter has a surface which converges angularly toward the socket. Successive pairs of such rings guide a needle point in the event that it impacts on the wall 29 of the throat upon being inserted into the needle cover for disposal. In the preferred embodiment, it is seen that a lip 31 is provided at the open mouth which if of a somewhat smaller diameter than the mouth opening. This is so that a needle not positioned coaxially but, rather at a skewed angle with respect to the axis of the socket and impacting upon the throat wall will not cause blood to spatter from the mouth of the needle cover. Preferably about the mouth there is a rim 33 of a somewhat larger diameter than the throat opening defining an end flange. In use, one inserts a needle and if not inserted correctly, the guide means composed of the throat will tend to center it and guard against "sticks" of the needle with the attendant possibility of causing germs to be transferred. Generally speaking, a needle cover has been provided for injection needles with the purpose of preventing or at least reducing the number of accidental self-puncture wounds among medical personnel who often are required to handle contaminated needles. This is for the purpose of reducing the spread of communicable diseases such as A.I.D.S. and hepititus as well as other infections from punctures in the health care community.

The needle covers which have been provided in the past have been ordinarily of about 4 to 6 centimeters in length and an approximately 5 millimeter inside diameter. This needle cover is molded of one piece rigid plastic which is relatively thick, especially in the throat area with an enlarged entrance or mouth opening of approximately about 3 centimeters. This funnel-type of throat allows extra protection by shielding a greater area of a person's hand while placing a needle into a needle cover. By reason of the guide means comprising the throat surface on insertion the needle tip is "caught" easily in the enlarged mouth and guided into the 5 millimeter socket opening. Preferably as is conventional, means are provided which cooperate with one another and which are a) on the interior of the needle socket, and b) the exterior of the barrel from which the needle projects and which maintain the needle, once in the socket, in the position shown in FIG. 2.

Preferably the exterior of the throat as shown in FIG. 2 is provided with knurling as at 32 to provide a gripping surface.

While the instant invention has been shown and described in what is to be considered a practical and preferred embodiment, it is recognized that departures may be made within the spirit and scope of this invention which is, therefore, not to be limited except as set forth in the claims which follow within the doctrine of equivalents.

What is claimed is:

1. A one-piece needle cover of rigid plastic material to receive and jacket a medical injection needle extending from one end of a needle barrel, said cover comprising:
   a. a generally tubular body having a closed end and an enlarged open end, said tubular body defining an elongate needle socket extending from the closed end a distance greater than the needle length to be received within said socket,
   b. means on the tubular body to nestingly engage the barrel and to cooperate with companionate means on the barrel to maintain the needle in said socket,
   c. said enlarged open end defining a mouth of at least about three centimeters in diameter, and
   d. said tubular body defining a throat converging towards the socket, said throat having guide means on the surface thereof to guide a needle being inserted into the cover, and said throat being provided with a surface stepped in successive rings each of a lesser diameter than the adjacent ring progressing from an outer largest diameter to a smaller diameter located at the socket.

2. A needle cover as set forth in claim 1 wherein some of said rings have a surface which converges toward the socket.

3. A needle cover as set forth in claim 1 wherein a lip is provided about the mouth and said lip is of a diameter slightly less than the diameter of the mouth to trap the point of a needle being inserted therein if not in coaxial alignment with the socket and the surface of the throat is contacted forceably by the needle point.

4. A needle cover as set forth in claim 1 wherein a rim is provided extending radially outwardly of said open mouth.

* * * * *